(12) United States Patent
Kraus et al.

(10) Patent No.: US 11,691,872 B2
(45) Date of Patent: *Jul. 4, 2023

(54) PORE FORMATION IN A SUBSTRATE

(71) Applicant: Applied Materials, Inc., Santa Clara, CA (US)

(72) Inventors: Philip Allan Kraus, San Jose, CA (US); Joseph R. Johnson, Redwood City, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/713,410

(22) Filed: Apr. 5, 2022

(65) Prior Publication Data

US 2022/0227622 A1 Jul. 21, 2022

Related U.S. Application Data

(60) Continuation of application No. 16/985,959, filed on Aug. 5, 2020, now Pat. No. 11,325,827, which is a
(Continued)

(51) Int. Cl.
*B81C 1/00* (2006.01)
*H01L 21/02* (2006.01)
(Continued)

(52) U.S. Cl.
CPC ......... *B81C 1/00087* (2013.01); *G01N 27/49* (2013.01); *G01N 33/48721* (2013.01); *H01L 21/0228* (2013.01); *H01L 21/302* (2013.01)

(58) Field of Classification Search
CPC .......................... B81C 1/00087; G01N 27/416
See application file for complete search history.

(56) References Cited

U.S. PATENT DOCUMENTS 7,075,161 B2    7/2006  Barth
7,104,113 B2 *  9/2006  Zribi .................. G01N 25/4813
                                                    73/25.05
(Continued)

FOREIGN PATENT DOCUMENTS

CN       103449355 A       12/2013
CN       102901763 B  *    6/2014
(Continued)

OTHER PUBLICATIONS

Liu, Zewen, et al., "Solid-State Nanopore-Based DNA Sequencing Technology", Journal of Nanomaterials, May 2016, pp. 1-13.
(Continued)

*Primary Examiner* — Cachet I Proctor
(74) *Attorney, Agent, or Firm* — Patterson + Sheridan, LLP

(57) ABSTRACT

Methods are provided for manufacturing well-controlled, solid-state nanopores and arrays thereof. In one aspect, methods for manufacturing nanopores and arrays thereof exploit a physical seam. One or more etch pits are formed in a topside of a substrate and one or more trenches, which align with the one or more etch pits, are formed in a backside of the substrate. An opening is formed between the one or more etch pits and the one or more trenches. A dielectric material is then formed over the substrate to fill the opening. Contacts are then disposed on the topside and the backside of the substrate and a voltage is applied from the topside to the backside, or vice versa, through the dielectric material to form a nanopore. In another aspect, the nanopore is formed at or near the center of the opening at a seam, which is formed in the dielectric material.

20 Claims, 7 Drawing Sheets

Related U.S. Application Data division of application No. 16/049,749, filed on Jul. 30, 2018, now Pat. No. 10,752,496.

(60) Provisional application No. 62/561,962, filed on Sep. 22, 2017.

(51) Int. Cl.
*G01N 33/487* (2006.01)
*G01N 27/49* (2006.01)
*H01L 21/302* (2006.01)

(56) References Cited

U.S. PATENT DOCUMENTS

| | | | | |
|---|---|---|---|---|
| 8,518,829 | B2* | 8/2013 | Dang | B82Y 15/00 438/584 |
| 9,017,937 | B1* | 4/2015 | Turner | C12Q 1/6869 435/6.1 |
| 2005/0102721 | A1 | 5/2005 | Barth | |
| 2005/0186629 | A1 | 8/2005 | Barth | |
| 2007/0020146 | A1 | 1/2007 | Young et al. | |
| 2012/0108068 | A1 | 5/2012 | Lytle | |
| 2012/0267729 | A1 | 10/2012 | Dang et al. | |
| 2013/0092541 | A1* | 4/2013 | Drndic | G01N 27/44791 204/627 |
| 2014/0045270 | A1 | 2/2014 | Shim et al. | |
| 2014/0246317 | A1* | 9/2014 | Mayer | G01N 33/48721 204/452 |
| 2014/0262820 | A1 | 9/2014 | Kuan et al. | |
| 2015/0069329 | A1 | 3/2015 | Jeon et al. | |
| 2015/0108008 | A1 | 4/2015 | Kwok et al. | |
| 2016/0231307 | A1* | 8/2016 | Xie | B01L 3/502715 |
| 2016/0313278 | A1* | 10/2016 | Knickerbocker | G01N 33/48721 |
| 2017/0263966 | A1* | 9/2017 | Lozada | H01M 8/1011 |

FOREIGN PATENT DOCUMENTS

| | | |
|---|---|---|
| CN | 102901763 B | 6/2014 |
| CN | 104458813 A | 3/2015 |
| CN | 106916737 A | 7/2017 |
| EP | 1526109 A2 | 4/2005 |
| JP | 2005125490 A | 5/2005 |
| JP | 2006-220793 A | 8/2006 |
| JP | 2015525114 A | 9/2015 |
| KR | 10-2012-0000520 A | 1/2012 |
| KR | 20130085644 A | 7/2013 |
| WO | 2011162582 A2 | 12/2011 |
| WO | 2016127007 A2 | 8/2016 |
| WO | 2016187519 A1 | 11/2016 |

OTHER PUBLICATIONS

Yanagi, Itaru, et al.."Fabrication of 3-nm-thick Si3N4 membranes for solid-state nanopores using the poly-Si sacrificial layer process", Scientific Reports, Oct. 2015, pp. 1-13.
Archer, Marie J., et al., "Fabrication and Characterization of Silicon Micro-Funnels and Tapered Micro-Channels for Stochastic Sensing Applications", Sensors, Jun. 2008, pp. 3848-3872.
Gadgil, V. J., et al., "Fabrication of nano structures in thin membranes with focused ion beam technology", Surface & Coatings Technology, Mar. 2009, pp. 2436-2441.
Kwok, Harold, et al., "Nanopore Fabrication by Controlled Dielectric Breakdown", Plos One, Mar. 2014, pp. 1-6.
Venkatesan, Bala Murali, et al., "Highly Sensitive, Mechanically Stable Nanopore Sensors for DNA Analysis", Advanced Materials, Jul. 2009, pp. 2771-2776.
Schneider, Gregory F., et al., "DNA translocation through Graphene Nanopore", Kavli Institute of Nanoscience, 2010, pp. 3163-3167.
Goto, Yusuke, et al., "Integrated solid-state nanopore platform for nanopore fabrication via dielectric breakdown, DNA-speed deceleration and noise reduction", Scientific Reports, Aug. 2016, pp. 1-8.
Dela Torre, Ruby, et al., "Fabrication and characterization of solid-state nanopore arrays for high-throughput DNA sequencing", Nanotechnology, Sep. 2012, pp. 1-6.
International Search Report and Written Opinion dated Dec. 4, 2018 for Application No. PCT/US2018/045758.
Zeng, Shuangshuang et al., "Rectification of protein translocation in truncated pyramidal nanopores", Nature Nanotechnology, Oct. 2019, pp. 1056-1062.
Chinese Office Action dated Dec. 2, 2020 for Application No. 201880060056.2.
Korean Office Action dated Mar. 25, 2021 for Application No. 10-2020-7011482.
Japanese Office Action dated Jun. 15, 2021 for Application No. 2020-516720.
Korean Office Action dated Oct. 13, 2021 for Application No. 10-2020-7011482.
Extended European Search Report dated Nov. 10, 2021 for U.S. Appl. No. 18/858,427.
Korean Office Action dated Apr. 19, 2022 for Application No. 10-2020-7011482.
Office Action for Japanese Application No. 2022-032068 dated Mar. 7, 2023.

* cited by examiner

PORE FORMATION IN A SUBSTRATE

CROSS-REFERENCE TO RELATED APPLICATIONS

This is a continuation application of U.S. patent application Ser. No. 16/985,959, filed Aug. 5, 2020, which is a divisional application of co-pending U.S. patent application Ser. No. 16/049,749, filed Jul. 30, 2018, which claims benefit of U.S. Provisional Patent Application Ser. No. 62/561,962, filed on Sep. 22, 2017, each of which is herein incorporated by reference in its entirety.

BACKGROUND

Field

Aspects disclosed herein relate to methods of manufacturing well-controlled, solid-state nanopores and arrays of well-controlled, solid-state nanopores in a substrate.

Description of the Related Art

Nanopores are widely used for applications such as deoxyribonucleic acid (DNA) and ribonucleic acid (RNA) sequencing. In one example, nanopore sequencing is performed using an electrical detection method, which generally includes transporting an unknown sample through the nanopore, which is immersed in a conducting fluid, and applying electric potential across the nanopore. Electric current resulting from the conduction of ions through the nanopore is measured. The magnitude of the electric current density across a nanopore surface depends on the nanopore dimensions and the composition of the sample, such as DNA or RNA, which is occupying the nanopore at the time. Different nucleotides cause characteristic changes in electric current density across nanopore surfaces. These electric current changes are measured and used to sequence the DNA or RNA sample.

Various methods have been used for biological sequencing. Sequencing by synthesis, or second generation sequencing, is used to identify which bases have attached to a single strand of DNA. Third generation sequencing, which generally includes threading an entire DNA strand through a single pore, is used to directly read the DNA. Some sequencing methods require the DNA or RNA sample to be cut up and then reassembled. Additionally, some sequencing methods use biological membranes and biological pores, which have shelf lives and must be kept cold prior to use.

Solid-state nanopores, which are nanometer-sized pores formed on a free-standing membrane such as silicon nitride or silicon oxide, have recently been used for sequencing. Current solid-state nanopore fabrication methods, such as using a tunneling electron microscope, focused ion beam, or electron beam, however, cannot easily and cheaply achieve the size and position control requirements necessary for manufacturing arrays of nanopores. Additionally, current nanopore fabrication methods are time consuming.

Therefore, there is a need in the art for improved methods of manufacturing a well-controlled, solid-state nanopore and arrays of well-controlled, solid-state nanopores.

SUMMARY

Methods are provided for manufacturing well-controlled, solid-state nanopores and arrays of well-controlled, solid-state nanopores. In one aspect, methods for manufacturing nanopores and arrays of nanopores exploit a physical seam. One or more etch pits are formed in a topside of a substrate and one or more trenches, which align with the one or more etch pits, are formed in a backside of the substrate. An opening is formed between the one or more etch pits and the one or more trenches. A dielectric material is then formed over the substrate, for example, by oxidation or atomic layer deposition, to fill the opening. Contacts are then formed or placed on the topside and the backside of the substrate and a voltage is applied from the topside to the backside of the substrate, or vice versa, through the dielectric material to form a nanopore. In another aspect, the nanopore is formed at or near the center of the opening at a seam, which is formed in the dielectric material.

In one aspect, a method for forming a nanopore is provided. The method generally includes providing a substrate having at least one feature on a topside and at least one feature on a backside aligned with the at least one feature on the topside and at least one opening between the at least one feature on the topside and the at least one feature on the backside, forming a dielectric material over the substrate to fill the at least one opening, the dielectric material having at least one seam formed therein, and exploiting the at least one seam to form at least one nanopore.

In another aspect, a method for forming a nanopore is provided. The method generally includes forming an etch pit on a topside of a substrate, forming a trench on a backside of the substrate, the trench being aligned with the etch pit, forming an opening between the etch pit and the trench, the opening connecting the etch pit and the trench, forming a dielectric material over the substrate to fill the opening, the dielectric material having a seam formed therein, and exploiting the seam to form a nanopore.

In yet another aspect, a substrate is disclosed. The substrate generally includes a plurality of topside features on a topside of the substrate, a plurality of backside features on a backside of the substrate, each of the plurality of features on the topside being aligned to each of the plurality of features on the backside, a plurality of openings connecting each of the plurality of topside features to each of the plurality of backside features, and a dielectric material formed over the substrate, the dielectric material in each of the topside features having a nanopore at or near a center of each of the plurality of openings.

In yet another aspect, a method for forming a nanopore is provided. The method generally includes forming a trench on a backside of the substrate, forming an etch pit on a topside of the substrate, the etch pit being formed over an etch-stop layer, the etch-stop layer forming a barrier between the trench and the etch pit, forming a dielectric material from the barrier, disposing one or more contacts on the topside and the backside of the substrate, and applying a voltage from the topside contact to the backside contact, or vice versa, through the dielectric material to form a nanopore.

In yet another aspect, a method for forming a nanopore is provided. The method generally includes providing a substrate having at least one feature on a topside and at least one feature on a backside aligned with the at least one feature on the topside and at least one opening between the at least one feature on the topside and the at least one feature on the backside, forming a dielectric material over the substrate to fill the at least one opening, and applying a voltage from the topside to the backside through the dielectric material to form at least one nanopore.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only exemplary aspects and are therefore not to be considered limiting of its scope, and may admit to other equally effective aspects.

To facilitate understanding, identical reference numerals have been used, where possible, to designate identical elements that are common to the figures. It is contemplated that elements and features of one aspect may be beneficially incorporated in other aspects without further recitation.

DETAILED DESCRIPTION

Methods are provided for manufacturing well-controlled, solid-state nanopores and arrays of well-controlled, solid-state nanopores. In one aspect, methods for manufacturing nanopores and arrays of nanopores exploit a physical seam. One or more etch pits are formed in a topside of a substrate and one or more trenches, which align with the one or more etch pits, are formed in a backside of the substrate. An opening is formed between the one or more etch pits and the one or more trenches. A dielectric material is then formed over the substrate, for example, by oxidation or atomic layer deposition, to fill the opening. Contacts are then formed or placed on the topside and the backside of the substrate and a voltage is applied from the topside to the backside of the substrate, or vice versa, through the dielectric material to form a nanopore. In another aspect, the nanopore is formed at or near the center of the opening at a seam, which is formed in the dielectric material.

Methods disclosed herein refer to formation of solid-state nanopores on a semiconductor substrate as an example. It is also contemplated that the disclosed methods are useful to form other pore-like structures on various materials, including solid-state and biological materials. Methods disclosed herein also refer to formation of frustum-shaped etch pits and trenches as an example; however, other etched features and any combinations thereof are also contemplated. For illustrative purposes, a silicon on insulator (SOI) substrate with a silicon oxide dielectric layer is described; however, any suitable substrate materials and dielectric materials are also contemplated. Additionally, methods disclosed herein refer to a topside and a backside of the substrate. The topside and backside generally refer to opposite sides of the substrate and do not necessarily require an upward or downward orientation. As such, it is contemplated that methods described herein are also useful for forming a nanopore through a vertical membrane by exploiting a seam thereon. Additionally, while the methods disclosed herein generally refer to exploiting a seam, it is also contemplated that the disclosed methods are useful for exploiting a gap to form a nanopore.

Figure 1:
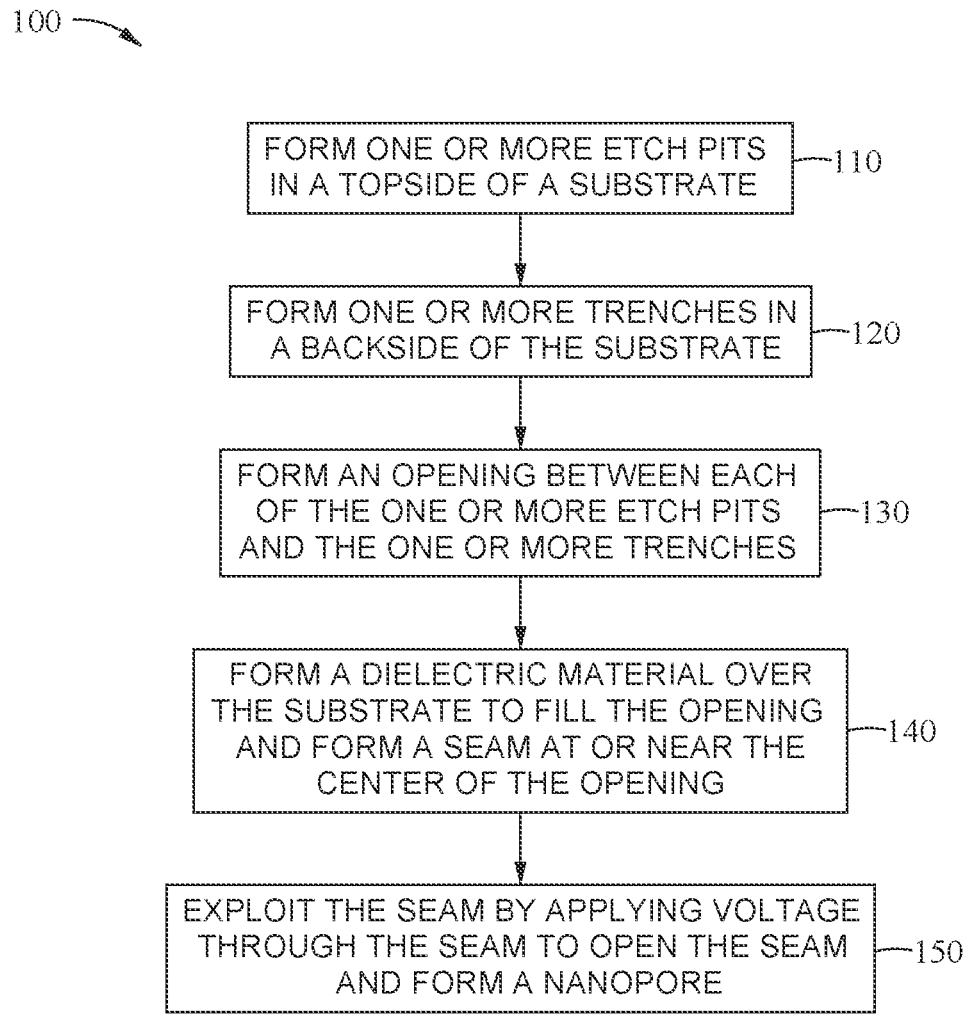
FIG. 1 is a process flow of a method for forming one or more nanopores according to the present disclosure.

FIG. 1 is a process flow of a method 100 for forming one or more nanopores according to the present disclosure.

Prior to method 100, a substrate is provided. The substrate is generally any suitable semiconductor substrate, such as a doped or undoped silicon (Si) substrate. The method 100 begins at operation 110 by forming one or more etch pits in a topside of a substrate. At operation 120, one or more trenches are formed in a backside of the substrate, which align with the one or more etch pits in the topside of the substrate. At operation 130, an opening is formed between each of the one or more etch pits and the one or more trenches. At operation 140, a dielectric material is formed over the substrate to fill the opening and form a seam at or near the center of the opening. The seam is generally formed at the intersection of the dielectric material formed on each of the sidewalls. At operation 150, the seam is exploited to form a nanopore by applying a voltage from the topside to the backside of the substrate, or vice versa, to open the seam and form the well-controlled nanopore.

In one aspect, operation 140 and operation 150 are part of stand-alone processes that are performed on an already-processed substrate having an opening therein.

Operation 120, operation 130, and operation 140 are generally performed in any suitable order. In one aspect, forming one or more trenches in the backside of the substrate at operation 120 occurs prior to forming one or more etch pits in the topside of the substrate at operation 110, and depositing the dielectric material at operation 140 is generally performed at any suitable stage of the method 100.

In one aspect, the substrate is oxidized to fill the opening and a seam is formed at or near the center of the opening in each of the one or more etch pits. In another aspect, a dielectric material is deposited over the substrate and a seam is formed at or near the center of the opening in each of the one or more etch pits. The dielectric material is generally deposited by any suitable deposition methods, including but not limited to, atomic layer deposition (ALD), physical vapor deposition (PVD), or chemical vapor deposition (CVD). Additionally, while some examples include formation of a seam in the deposited dielectric material, it is also contemplated that the dielectric material does not have a seam and that applying a voltage across the dielectric material at voltage sufficient to cause dielectric breakdown will form a nanopore within the dielectric material.

In another aspect, the method 100 further includes forming an etch stop layer at the bottom of the one or more etch pits in the topside of the substrate, for example, before oxidizing the substrate or depositing the dielectric material.

Figure 2A:
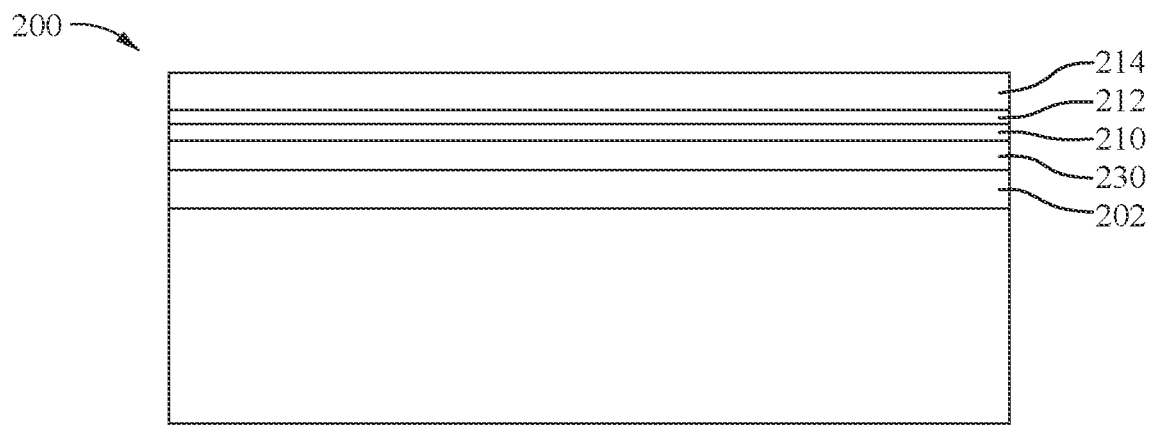
FIGS. 2A-2O depict cross-sectional views of a substrate in which one or more nanopores are formed at various stages of a process flow disclosed herein.
Figure 2B:
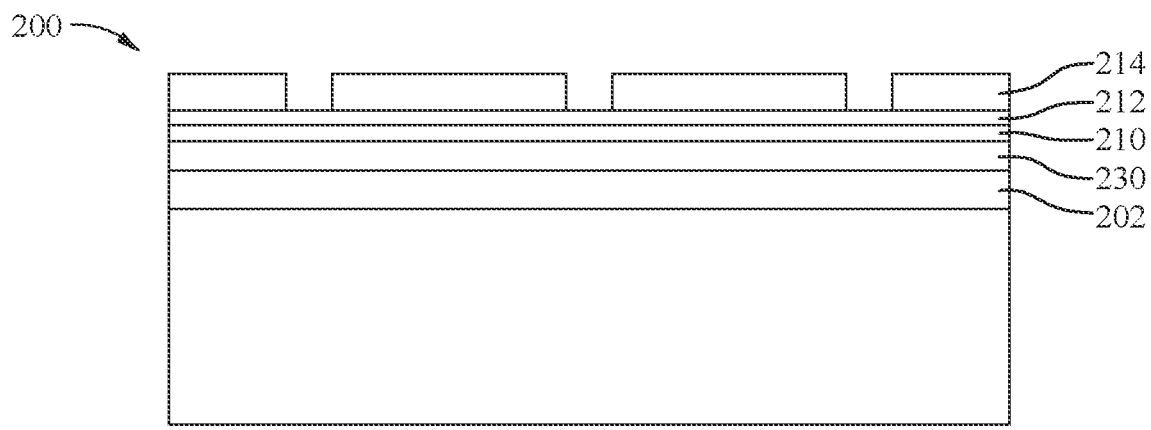
Figure 2C:
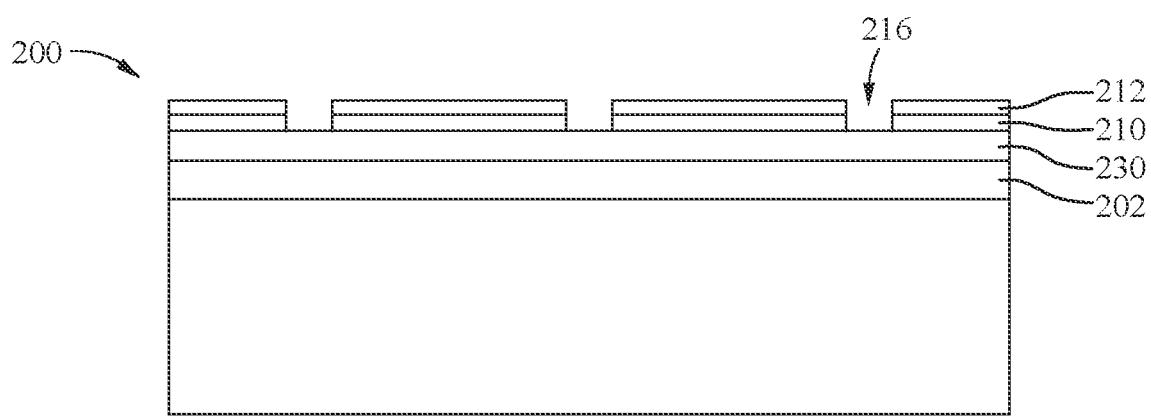
Figure 2D:
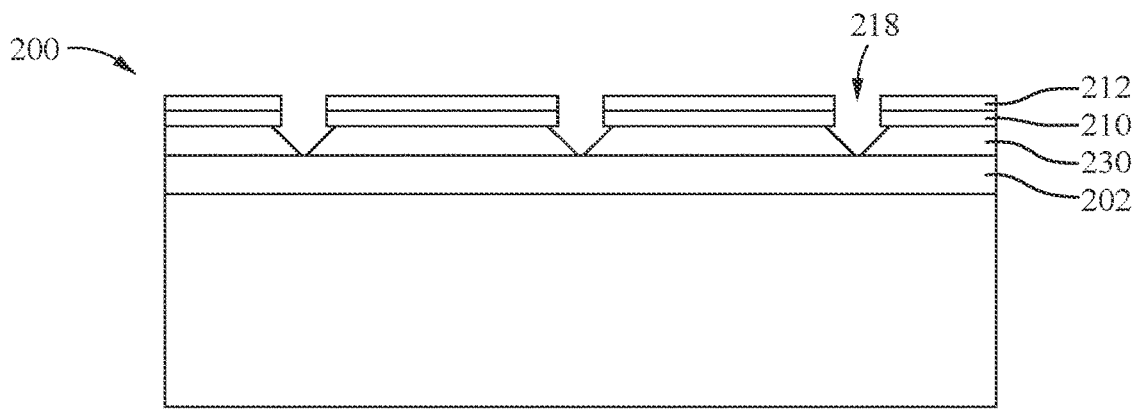
Figure 2E:
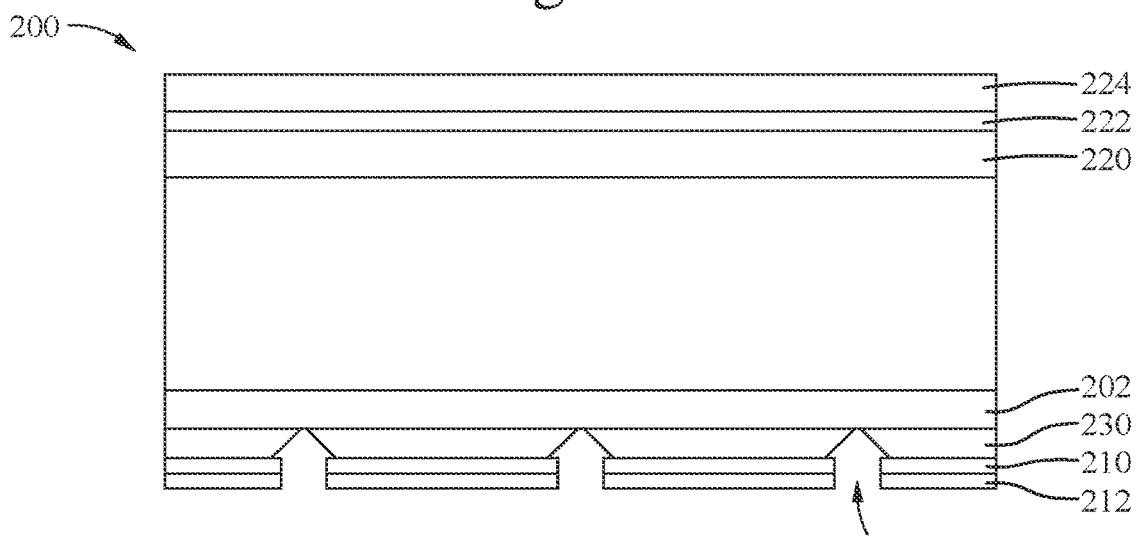
Figure 2F:
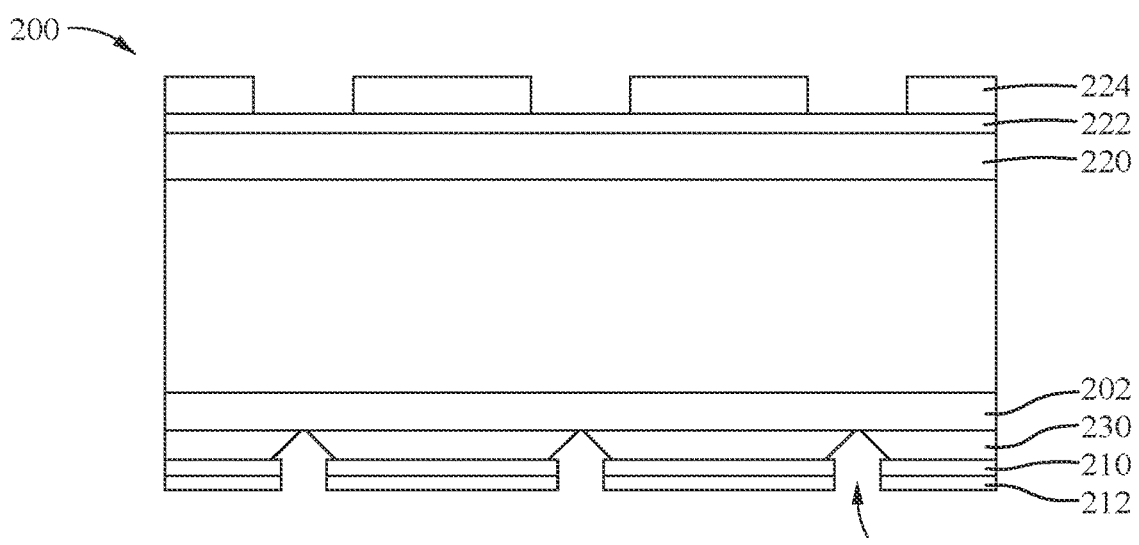
Figure 2G:
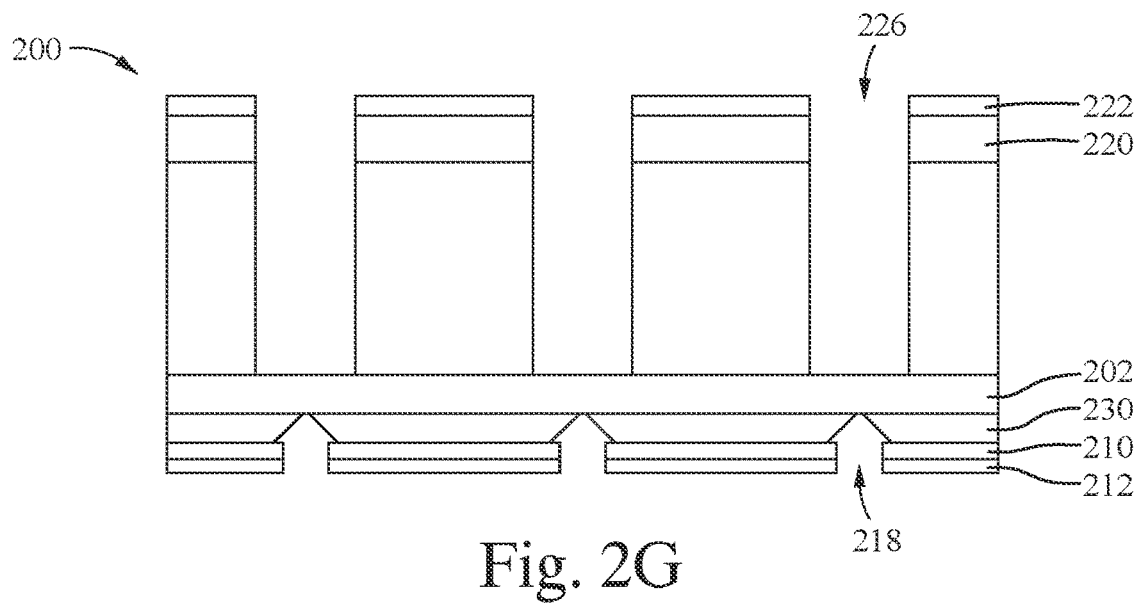
Figure 2H:
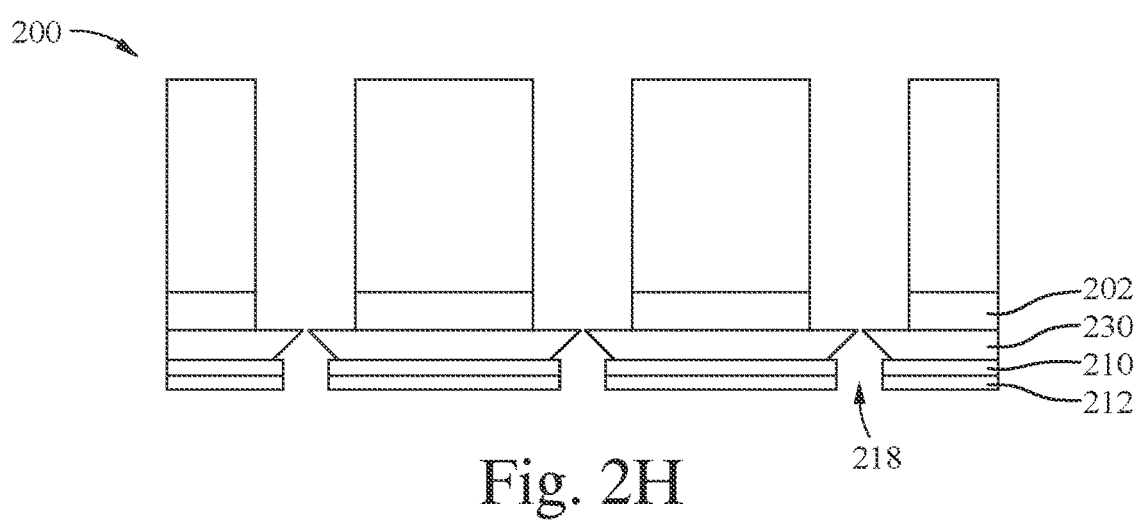
Figure 2I:
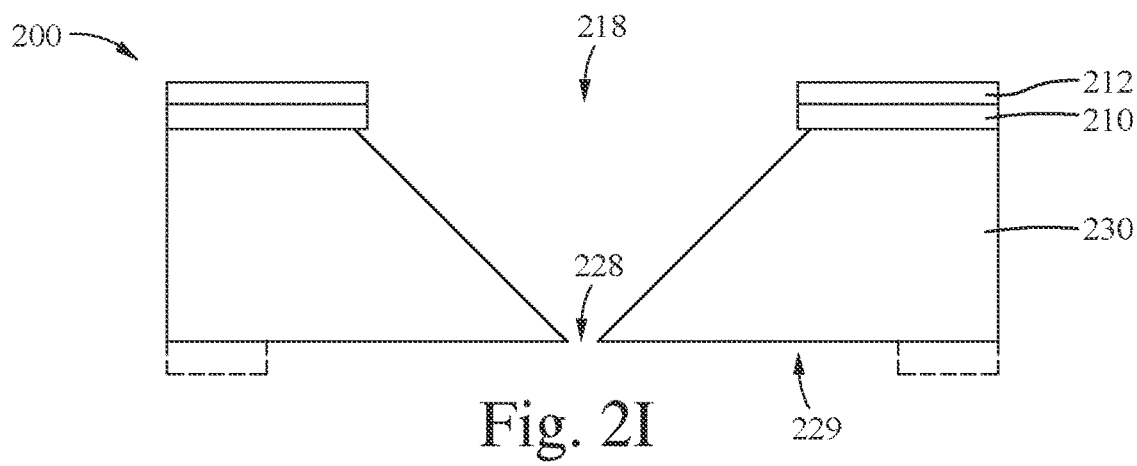
Figure 2J:
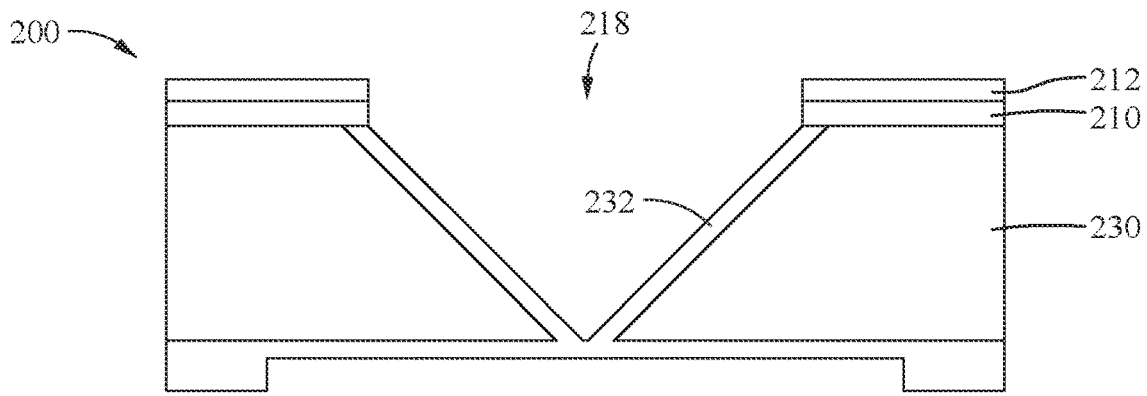
Figure 2K:
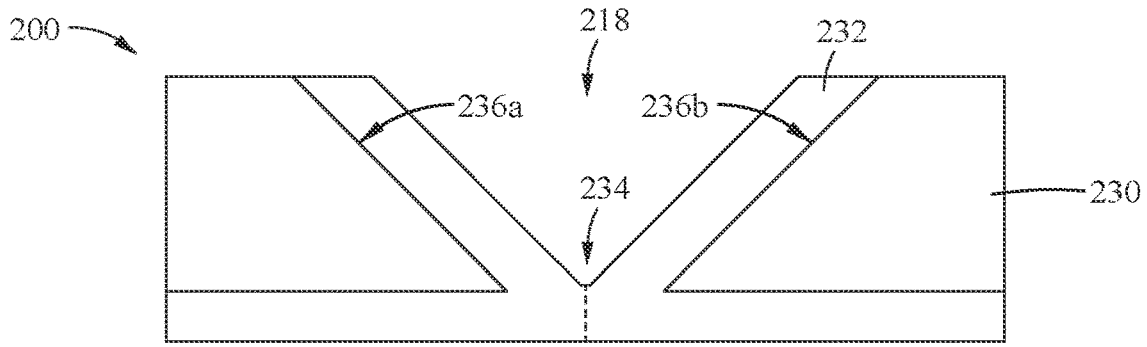
Figure 2L:
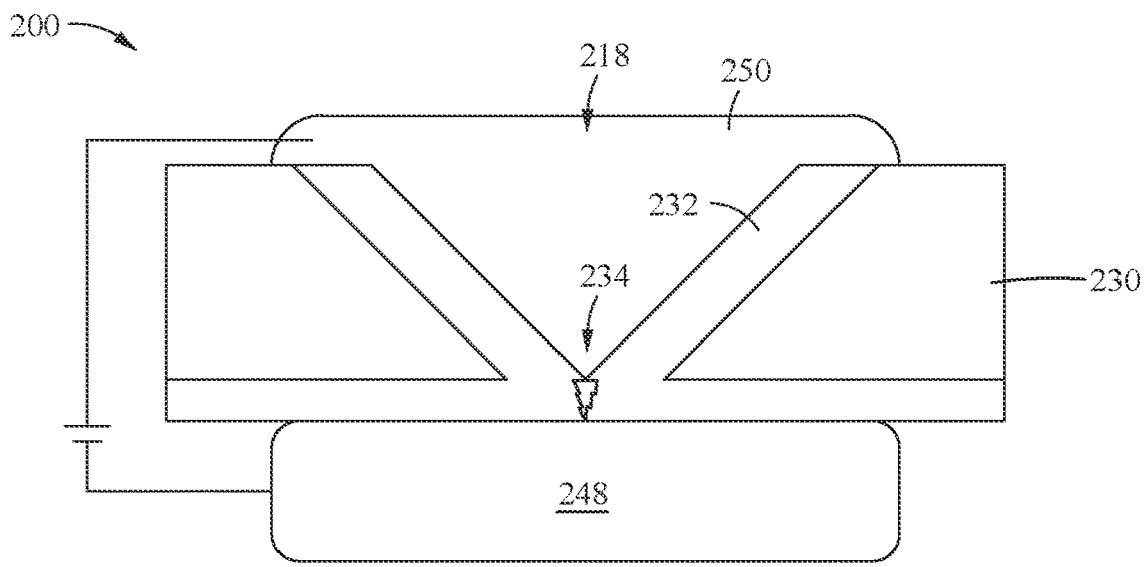
Figure 2M:
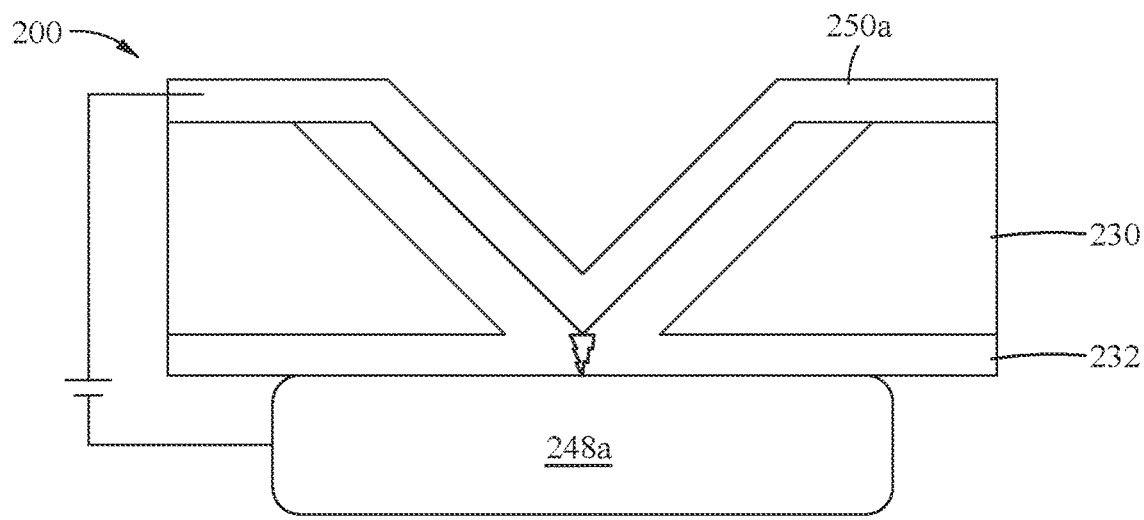
Figure 2N:
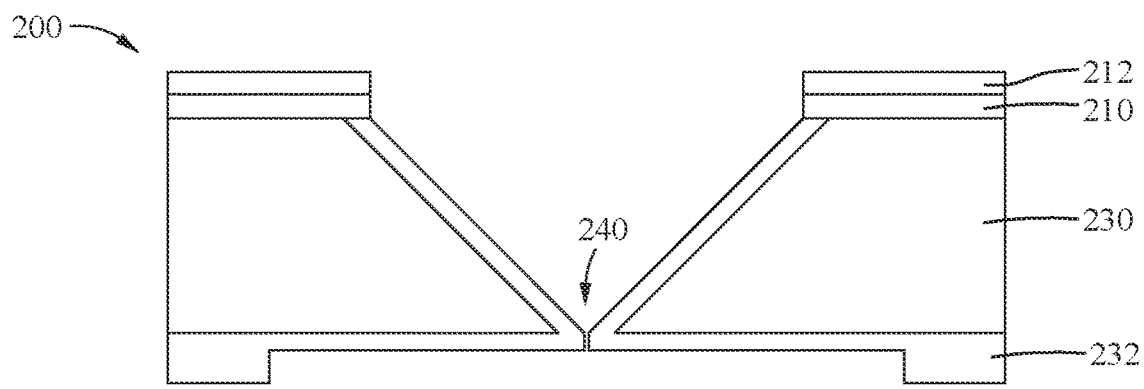
Figure 2O:
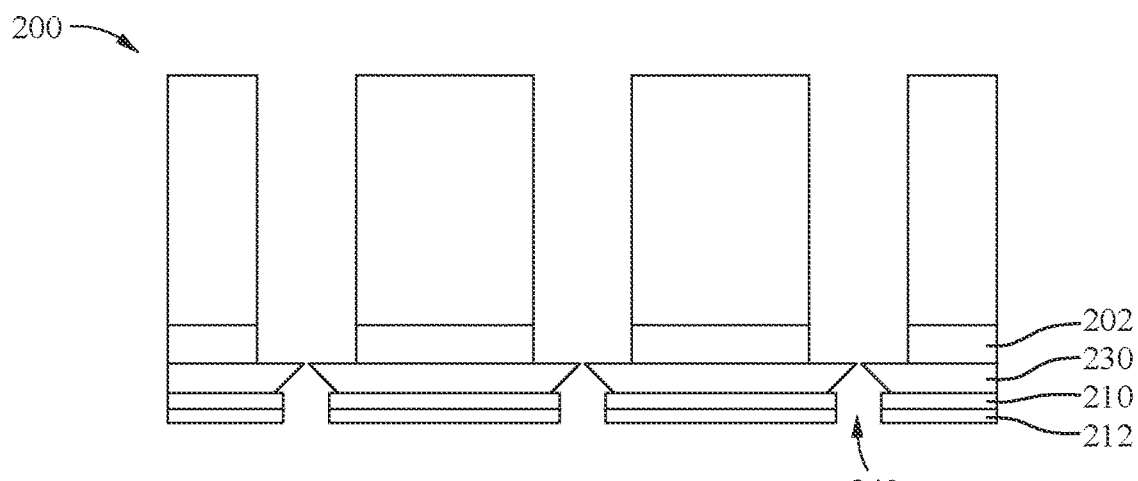

FIGS. 2A-2O depict cross-sectional views of a substrate 200 in which one or more nanopores are formed according to a method disclosed herein, such as at various stages of the method 100. While FIGS. 2A-2O are shown in a particular sequence, it is also contemplated that the various stages of method 100 depicted in FIGS. 2A-2O are performed in any suitable order.

As shown in FIG. 2A, a topside hard mask 210 is disposed over a topside of the substrate 200, a topside bottom anti-reflective coating (BARC) layer 212 is disposed over the topside hard mask 210, and a topside photoresist 214 is disposed over the topside BARC layer 212. A topside patterning process is then performed to form one or more trenches 216 in the topside hard mask 210 and the topside BARC layer 212. Generally, the topside patterning process includes patterning the topside photoresist 214, as shown in FIG. 2B, and then etching, for example by reactive ion etching (RIE), the unmasked topside hard mask 210 and topside BARC layer 212, as shown in FIG. 2C. The topside photoresist 214 is optionally removed. A topside etch process, such as a KOH etch or other suitable etch process, is then performed to form one or more frustum-shaped etch pits 218 in the substrate 200, as shown in FIG. 2D. Other suitable etch processes include, but are not limited to, anisotropic etch processes.

The substrate 200 is then flipped for backside processing. As shown in FIG. 2E, a backside hard mask 220 is deposited over a backside of the substrate 200, a backside BARC layer 222 is deposited over the backside hard mask 220, and a backside photoresist 224 is deposited over the backside BARC layer 222. A backside patterning process is then performed to form one or more backside trenches 226 in the backside hard mask 220 and the backside BARC layer 222. Generally, the backside patterning process includes patterning the backside photoresist 224, as shown in FIG. 2F, and then etching the unmasked backside hard mask 220, backside BARC layer 222, and a portion of the substrate 200 to form the one or backside trenches 226, as shown in FIG. 2G. The spin coated backside photoresist 224 is optionally removed.

In the aspect of FIGS. 2A-2O, the substrate 200 is an SOI substrate having a buried oxide layer 202 therein with a 150 nanometer (nm) Si device layer 230 on the topside thereof as an example; however, any suitable substrate or SOI substrate is also contemplated. The topside hard mask 210 is a low-pressure chemical vapor deposition (LPCVD) nitride, and the topside photoresist 214 is a spin coated photoresist. The one or more frustum-shaped etch pits 218 are generally any suitable size based on the size of the substrate. For example, in an aspect in which an SOI substrate having 150 nm Si device layer on a topside thereof is used, the one or more frustum-shaped etch pits 218 are 212 nanometer (nm) by 212 nm square openings spaced at 5 millimeter (mm) pitch. A KOH etch generally etches Si at an angle of about 54.7 degrees. Accordingly, when the topside KOH etch is performed on the SOI substrate 200 for a predetermined period of time, the one or more frustum-shaped etch pits 218 generally terminate with a tip of the frustum-shaped etch pit 218 on and in contact with the buried oxide layer 202. The predetermined period of time is generally determined to reduce or eliminate lateral etch relative to the mask opening. In general, the <100> plane 229 of the Si, shown in FIG. 2I, will etch at a rate that corresponds to the temperature of the solution and the concentration of KOH in $H_2O$. For most scenarios, KOH will etch the <100> plane of Si at a rate of between about 0.4 nm/s and about 20 nm/s. The rate can be accelerated or retarded by cooling or heating the solution.

Patterning the backside photoresist 224 includes forming a pattern of openings of any suitable size and shape, which are aligned with the one or more frustum-shaped etch pits 218. For example, in an aspect in which an SOI substrate having 150 nm Si device layer on a topside thereof is used, as discussed above, the backside photoresist 224 is patterned with 100 micrometer (μm) by 100 μm square openings at 5 mm pitch, which are aligned with the one or more frustum-shaped etch pits 218 on the topside of the substrate 200. In one aspect, a deep reactive ion etch (DRIE) is then used to form the one or more backside trenches 226. The one or more backside trenches 226 are etched down to the backside surface of the buried oxide layer 202 such that the bottom of each of the one or more backside trenches 226 corresponds to the top of the buried oxide layer 202, as shown in FIG. 2G. A local removal process, such as a hydrofluoric acid (HF) dip, is then used to remove the buried oxide layer 202 in the one or more backside trenches 226 such that a bottom of each of the one or more backside trenches 226 is on and in contact with the device layer 230 and an opening 228 is formed at the tip of the one or more frustum-shaped etch pits 218, as shown in FIG. 2I, which is an enlarged and inverted portion of FIG. 2H. In further aspects, wet etch processes are used to form the one or more backside trenches 226.

Generally, the size of the opening 228 is controlled by controlling the chemistry, temperature, concentration gradients, and byproduct removal gradients during the etch processes. In one aspect, the opening is between about 5 nm by 5 nm and about 10 nm by 10 nm. The size of the opening is generally measured using a scanning electron microscope (SEM) or a transmission electron microscope (TEM).

A dielectric material 232 is then formed over the substrate 200 to fill the opening 228, as shown in FIG. 2J. The thickness of the dielectric material 232 is generally between about 0.5 nm to about 10 nm, for example between about 1 nm and about 5 nm, such as about 1 nm. In one aspect, the silicon device layer of the SOI substrate 200 is oxidized, for example by exposing the substrate to oxygen or water ($H_2O$) to form the dielectric material 232. In another aspect, the dielectric material 232 is deposited by ALD. In another aspect, the dielectric material 232 is formed by depositing a metal or semiconductor layer, for example, by ALD, CVD, or PVD, and then oxidizing the metal or semiconductor layer to form a dielectric material. As shown in FIG. 2K, which is an enlarged portion of FIG. 2J, a seam 234 is formed in the dielectric material 232 at or near the center of the opening 228, where the dielectric material 232 formed on the sidewalls 236a, 236b of the frustum-shaped etch pits 218 comes together. When oxidation of the silicon device layer is used, for example, the opening 228 is closed by the volume expansion when the silicon (Si) is converted to silicon dioxide ($SiO_2$). The seam 234 is a weak point in the dielectric material 232.

The seam 234 is then exploited to form a well-controlled nanopore 236. Generally, exploiting the seam 234 includes applying a voltage from a top contact over the dielectric material 232 on a topside of the substrate 200 to a bottom contact over the dielectric material 232 on the backside of the substrate 200, or vice versa, through the seam 234. The applied voltage induces dielectric breakdown of the oxide at the seam 234, forming a well-controlled, localized and robust nanopore at the location of the seam 234, which is generally at or near the center of the opening 228. The applied voltage generally removes at least a portion of the dielectric material 232 to form the nanopore, for example, by degrading a portion of the dielectric material 232. The applied voltage generally includes typical voltages above the breakdown voltage of the dielectric material. For example, the breakdown voltage of $SiO_2$ is generally between about 2 megavolts (MV)/cm and about 6 MV/cm, or between about 200-600 millivolts (mV)/nm of material. In one aspect, the applied voltage is slightly below the breakdown voltage of the dielectric material and the current is applied for longer to slowly break down the membrane. In another aspect, the applied voltage is above the breakdown voltage of the dielectric material such that a nanopore is blasted therethrough.

In one aspect, the top contact 250 is disposed in a first electrolyte on the topside of the substrate 200 and the bottom contact 248 is disposed in a second electrolyte on the backside of the substrate 200, as shown in FIG. 2L. In one example, the top contact 250a and/or the bottom contact 248a is a conductive tungsten (W) layer, as shown in FIG. 2M. In further aspects, the top and bottom contacts are any suitable conductive material, such one or more metals or combinations thereof.

Once the voltage has been conducted through the seam 234, a nanopore 240 is formed at or near the center of the opening 228, as shown in FIG. 2N. Because the nanopore 240 has been formed according to methods disclosed herein, the size and position of the nanopore 240 are well controlled. A well-controlled size of the nanopore 240 is generally a diameter suitable for sequencing a sample of a certain size. In one aspect, the size of the nanopore 240 is about 100 nm or less. In one aspect, the size of the nanopore 240 is between about 0.5 nm and about 5 nm, for example between about 1 nm and about 3 nm, such as 2 nm. In another aspect, the size of the nanopore 240 is between about 1.5 nm and about 1.8 nm, such as about 1.6 nm, which is roughly the size of a single strand of DNA. In another aspect, the size of the nanopore 240 is between about 2 nm and about 3 nm, such as about 2.8 nm, which is roughly the size of double-stranded DNA. A well-controlled position of the nanopore 240 is generally any position on the substrate which is suitable for configuration of one or more nanopores. In one aspect, the substrate 200 includes an array of nanopores 240, as shown in FIG. 2O. Methods disclosed herein are generally used to control the position of each of the one or more nanopores 240 such that a nanopore array of desired configuration for sequencing or other processes is formed.

In one aspect using a tungsten layer, the tungsten is generally patterned to be addressable to each nanopore such that an array of nanopores for sequencing is formed. In another aspect, the voltage is applied sequentially to each feature to form an array of nanopores for sequencing.

As disclosed above, the stages depicted in FIGS. 2A-2O are generally performed in any suitable order. In one aspect, the one or more etch pits 218 are formed and then a thin layer of dielectric material 232 is conformally deposited over the one or more etch pits 218. Then, the one or more backside trenches 226 are formed and the buried oxide layer 202 is preferentially removed such that a free-standing dielectric layer remains. A voltage is then applied across the dielectric material 232 to form one or more nanopores 240, as disclosed above.

In this aspect, a thickness of the conformal dielectric material 232 is between about 0.5 nm and about 10 nm, for example between about 0.5 nm and about 5 nm, for example between about 1 nm and about 2 nm, such as about 1 nm. The dielectric material 232 is generally any suitable dielectric material with an etch rate that is low relative to $SiO_2$. Examples of suitable dielectric materials include, but are not limited to, $Al_2O_3$, $Y_2O_3$, $TiO_2$, and SiN. The etch rate of the dielectric material 232 compared to the etch rate of $SiO_2$ is generally greater than about 10:1, for example about 100:1, for example about 1,000:1, for example about 10,000:1. A seam may or may not be formed at the center of the opening 228 at the bottom of the etch pit 218. However, voltage may still be applied across the dielectric material 232 such that a nanopore 240 is formed at a weak point in the dielectric material 232.

Figure 3A:
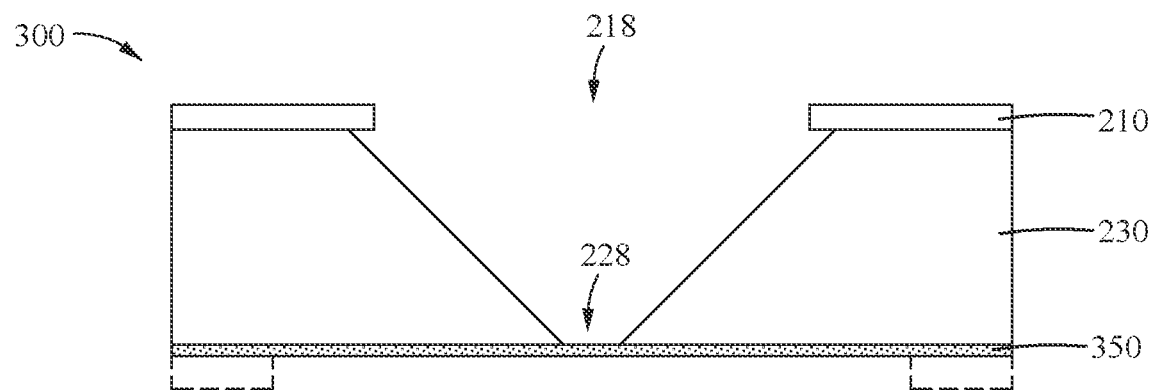
FIGS. 3A-3C depict cross-sectional views of a substrate in which one or more nanopores are formed at various stages of another process flow disclosed herein.
Figure 3B:
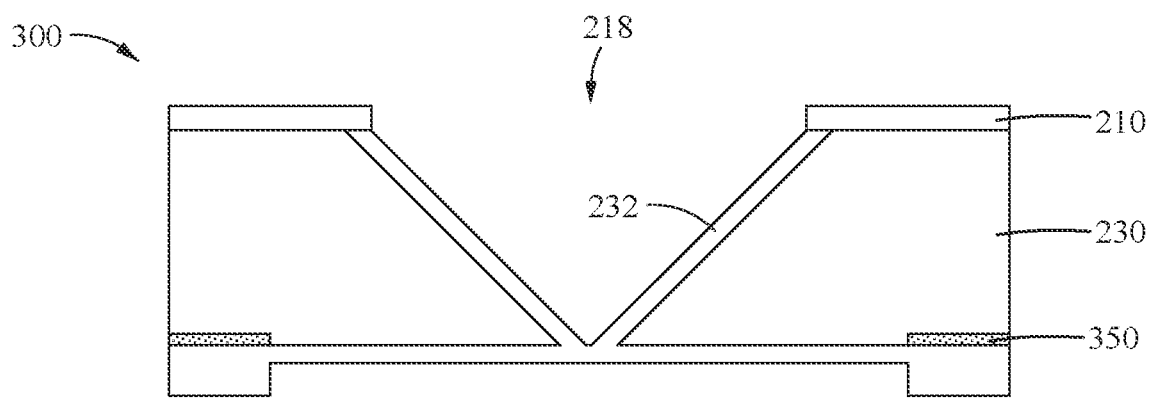
Figure 3C:
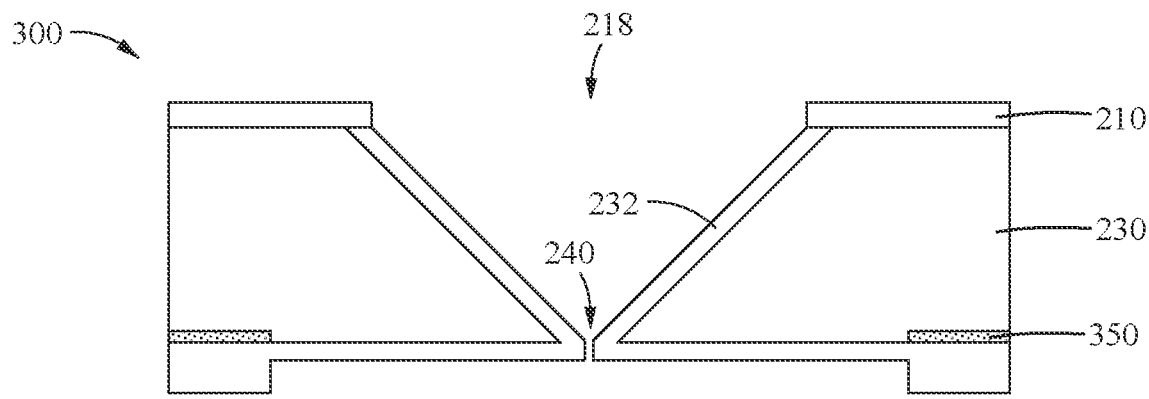

FIGS. 3A-3C depict cross-sectional views of a substrate 300 in which one or more nanopores are formed according to a process flow disclosed herein, such as at various stages of the method 100. The stages depicted in FIGS. 3A-3B are alternative stages of nanopore formation in the substrate, which may be substituted into the various stages depicted in FIGS. 2A-2O and disclosed above.

In the aspect depicted in FIGS. 3A-3C, an etch-stop layer 350 is disposed at the bottom of the one or more etch pits 218, as shown in FIG. 3A. The etch-stop layer 350 causes the KOH etch to stop at the bottom of the etch pit 218 at a well-controlled thickness. An opening 228 still exists at the bottom of the etch pit 218 at the thin, exposed etch-stop layer 350. The substrate 300 is then oxidized to form a well-controlled oxide layer, such as a layer of dielectric material 232, for example by rapid thermal processing (RTP) oxidation, to close the opening 228, as shown in FIG. 3B. A voltage is then applied across the dielectric material 232, causing dielectric breakdown within the area of the opening 228 at the base of the etch pit 218 such that a nanopore 240 is formed within the opening 228, as shown in FIG. 3C. According to this aspect, a seam may or may not be formed in the dielectric material 232; however, dielectric breakdown at a weak point in the dielectric material 232 at the base of the etch pit 218 will still form the nanopore 240.

The etch-stop layer 350 is deposited by any suitable method at any suitable stage of the process flows disclosed herein. In one aspect, the etch-stop layer 350 is formed by implanting or diffusing dopants into the silicon device layer and in contact with the buried oxide layer 202 of the SOI substrate during SOI substrate manufacturing. In another aspect, the etch-stop layer 350 is formed after the one or more backside trenches 226 are formed in the backside of the substrate 300 and prior to the formation of the one or more etch pits 218 in the substrate 300. The thickness of the etch-stop layer is any suitable thickness, such as, less than or equal to 10 nm, for example less than or equal to 2 nm, for example less than or equal to 1 nm. The etch-stop layer 350 generally includes any suitable dopant, including but not limited to, boron (B).

The thickness of the oxidation is any suitable thickness, such as between about 0.5 nm and about 10 nm, for example between about 1 nm and about 5 nm, for example about 1 nm.

Benefits of the present disclosure include the ability to quickly form well-controlled nanopores and nanopore arrays, which are generally individually addressable. Disclosed methods generally provide nanopores that are well-controlled in size and in position through a thin film membrane. Methods of manufacturing nanopores of well-controlled size provide improved signal-to-noise ratios because the size of the nanopore is similar to the size of the sample, such as a single strand of DNA, being transmitted through the nanopore, which increases the change in electric current passing through the nanopore. Additionally, methods of manufacturing nanopores having well-controlled positions enables a sample, such as DNA, to freely pass through the nanopore. Additionally, the thinness of the membrane, for example, about 1 mm, provides for improved reading of the DNA sequence.

While the foregoing is directed to aspects of the present disclosure, other and further aspects of the disclosure may be devised without departing from the basic scope thereof, and the scope thereof is determined by the claims that follow.

What is claimed is:

1. A substrate comprising:
   a buried oxide layer;
   a device layer disposed on the buried oxide layer;
   a hard mask disposed on the device layer;
   a plurality of topside features on a topside of the substrate, the plurality of topside features being frustum-shaped etch pits;
   a plurality of backside features on a backside of the substrate, each of the plurality of topside features being aligned to each of the plurality of backside features;
   a plurality of openings connecting each of the plurality of topside features to each of the plurality of backside features; and
   a dielectric material formed over the substrate, the dielectric material in each of the topside features having a nanopore at or near a center of each of the plurality of openings.

2. The substrate of claim 1, wherein a diameter of the nanopore is less than or equal to 100 nanometers.

3. The substrate of claim 2, wherein the diameter of the nanopore is between about 1 nanometer and about 2 nanometers.

4. The substrate of claim 1, wherein the plurality of backside features are trenches.

5. The substrate of claim 1, wherein an etch-stop layer is disposed at a bottom of each of the frustum-shaped etch pits.

6. The substrate of claim 1, wherein the device layer is a silicon containing device layer and has a thickness of about 150 nanometers.

7. The substrate of claim 1, wherein the substrate is a silicon-on-insulator substrate.

8. A substrate comprising:
a buried oxide layer;
a device layer disposed on the buried oxide layer;
a plurality of topside features formed through the device layer;
a plurality of backside features formed through at least the buried oxide layer;
a nanopore connecting each of the plurality of topside features to each of the plurality of backside features; and
a dielectric material formed over a surface of the device layer and within the nanopore and between the topside features and the backside features.

9. The substrate of claim 8, wherein the plurality of topside features are frustum-shaped etch pits.

10. The substrate of claim 9, wherein an etch-stop layer is disposed at a bottom of each of the frustum-shaped etch pits.

11. The substrate of claim 8, wherein the dielectric material is formed over each of the plurality of topside features.

12. The substrate of claim 8, wherein a thickness of the dielectric material is about 0.5 nanometers to about 10 nanometers and the nanopore has a diameter of about 0.5 nm to about 5 nm.

13. The substrate of claim 8, wherein the dielectric material comprises one or a combination of Al2O3, Y2O3, TiO2, and SiN.

14. The substrate of claim 8, wherein the substrate is a silicon-on-insulator substrate.

15. A substrate comprising:
a buried oxide layer;
a device layer disposed on the buried oxide layer;
a plurality of topside features formed through the device layer, the plurality of topside features being frustum-shaped etch pits;
a plurality of backside features formed through at least the buried oxide layer, wherein the plurality of backside features are trenches, each of the of the plurality of topside features being aligned to each of the plurality of backside features;
a nanopore connecting each of the plurality of topside features to each of the plurality of backside features; and
a dielectric material formed over sidewalls of the frustum-shaped etch pits and within the nanopore and between the topside features and the backside features.

16. The substrate of claim 15, wherein an etch-stop layer is disposed at a bottom of each of the frustum-shaped etch pits.

17. The substrate of claim 15, wherein a thickness of the dielectric material is about 0.5 nanometers to about 10 nanometers and the nanopore has a diameter of about 0.5 nm to about 5 nm.

18. The substrate of claim 15, wherein the dielectric material comprises one or a combination of Al2O3, Y2O3, TiO2, and SiN.

19. The substrate of claim 15, wherein the substrate is a silicon-on-insulator substrate.

20. The substrate of claim 19, wherein the device layer is a silicon containing device layer.

* * * * *